United States Patent [19]
Adams

[11] Patent Number: 6,055,873
[45] Date of Patent: May 2, 2000

[54] METHOD AND MEANS FOR DETERMINING THE COMPOSITION OF FLUIDIZABLE SOLID MATTER PARTICLES

[75] Inventor: Horst Adams, St. Gallen, Switzerland

[73] Assignee: Wagner International AG, Alstatten, Switzerland

[21] Appl. No.: 09/248,773

[22] Filed: Feb. 12, 1999

[30] Foreign Application Priority Data

Mar. 16, 1998 [DE] Germany ............................ 198 11 341

[51] Int. Cl.[7] .................................................. G03G 21/00
[52] U.S. Cl. ............................................................ 73/865.5
[58] Field of Search .............................. 73/865.5, 865.8; 324/652, 655, 656, 653, 675, 672

[56] References Cited

U.S. PATENT DOCUMENTS 5,909,609   6/1999   Yahata et al. .

Primary Examiner—Robert Raevis
Attorney, Agent, or Firm—Fenwick & West LLP

[57] ABSTRACT

The invention provides a method for determining the composition of fluidizable solid matter particles, such as powder particles, in which the solid matter particles are fed through a measuring resonator device comprising a high frequency resonator under defined feeding conditions, and a change of the resonant frequency and/or the amplitude of the high frequency resonator is detected in the measuring resonator means, said change being caused by the fed solid matter particles.

16 Claims, 3 Drawing Sheets

METHOD AND MEANS FOR DETERMINING THE COMPOSITION OF FLUIDIZABLE SOLID MATTER PARTICLES

BACKGROUND OF THE INVENTION

The invention relates to a method and an apparatus for determining the composition of free-flowing or fluidizable solid matter particles, which may be for instance powdery or granular, in particular for determining the composition of a color powder. The invention in particular relates to the determination of the composition of a coating powder for an electrostatic powder coating apparatus with respect to its average particle size and physical and/or chemical properties.

With the increasing quality demands of powder coating technology the demands on quality of the coating powder to be processed also rise continuously. Modern powder coating apparatus and devices may be adjusted precisely to the coating powder to be sprayed in order to reach an optimum coating quality. In order to ensure a constant quality, it is necessary to maintain a quality level achieved by a certain adjustment without interruption over a long period of time.

The supply means and coating devices are developed continually and permit more specific adjustments, for instance an adjustment of the powder supply so that with a certain powder quality a predetermined or maximum flow rate at an optimum electrostatic charging of the coating powder is achieved. The powder quality is reflected for instance by the average particle size, the grain size distribution and/or the chemical properties of the powder. Since the supply means and coating devices are precisely adjusted to the respective powder quality, fluctuations in quality of the coating powder have a very strong influence on the final coating quality. Quality fluctuations of that kind in particular occur when a new powder batch is used.

The methods of the prior art of inspecting the coating powder take a relatively long time and involve expensive chemical analysis and/or physical tests, e.g. for determining the particle size distribution of the powder. In order to ensure a constant coating quality, these tests would always have to be conducted before use of a new powder batch, which is not practical for time and cost reasons.

SUMMARY OF THE INVENTION

Thus, there is a need for a means and a method of characterizing the composition of a coating powder in a quick and simple manner to supply to an operator of a powder coating device at least the information whether the composition of the coating powder has changed with respect to a previous powder batch. If a change in powder quality was detected, the appropriate corrections at the adjustment of the powder coating apparatus can be made by the operator of the powder coating device, and the batch can be rejected during input inspection.

The detected change of the resonant frequency and/or the radio frequency amplitude of the high frequency resonator may for instance be compared to appropriate values, which are derived from the empty measuring resonator device.

The solid matter particles are preferably supplied at a predetermined supply air quantity and dosing air quantity according to the Venturi principle.

The invention also provides a means for determining the composition of fluidizable solid matter particles, such as color powder, comprising a supply device for supplying the solid matter particles under defined supply conditions, and comprising a measuring resonator device which has a high frequency resonator to detect a change of the resonant frequency and/or of the amplitude of the resonant frequency resonator, said change being caused by the supplied solid matter particles. The measuring resonator device specifically comprises a comparator in order to deliver an indication on whether the natural frequency and/or the RF amplitude of the high frequency resonator when supplying the solid matter particles of a second test quantity has change with respect to a first test quantity.

The solid matter particles can be supplied to the measuring resonator device through a funnel device at a constant rate per time unit. A more precise result is, however, obtained when a Venturi injector is used having a feed air supply for supplying the solid matter particles to the measuring resonator device. The Venturi injector preferably also has a dosing air supply. A control means for adjusting a defined supply air quantity and/or dosing air quantity can be provided, which is connected to the feed air supply and the dosing air supply.

The invention preferably uses the high frequency resonator, which is known from the German patent applications DE 44 40 046 and DE 196 50 112, in which it is used for powder density determination. The two patent applications are incorporated herein by reference.

A certain powder quantity per time is pneumatically supplied through the high frequency resonator under precisely defined conditions. The feeding operation is preferably performed by a Venturi injector, wherein the supply air and possibly the dosing air are precisely measured and controlled. Suitable air control modules are described in the German patent application 197 13 668.0, which is incorporated herein by reference.

When the powder flows through the high frequency resonator, a shift of the resonant frequency and a change of the RF amplitude of the resonator result when compared to the empty resonator or compared to a reference value. The frequency shift is in particular suitable as a characterization feature for a certain powder, i.e. it is made use of the fact that powders having different compositions cause different frequency shifts at equal feeding conditions.

The reason for this is to be seen in the measuring method: the magnitude of the frequency shift is proportional to the dielectricity constant of the power, and to the density of the powder in the resonator volume. Two effects are utilized:

1) when a physical and/or chemical composition of the powder changes, the dielectricity constant changes;
2) when the grain size spectrum, i.e. the distribution of the particle sizes of the powder changes, the density of the powder (i.e. the number of particles per $cm^3$) in the resonator changes at constant feeding and marginal conditions (in particular at constant supply and dosing air).

Both effects lead individually and in combination to a frequency shift and to a change of the amplitude, the evaluation of which, however, requiring more effort.

The method according to the invention is not only suitable for determining the composition of a coating powder, but also for determining any other material of fluidizable or flowing solid matter particles, which can be powdery or granular and which can be supplied through a measuring line and the measuring resonator device under defined, constant conditions. It can be easily and quickly determined by the invention, whether the composition of the supplied material has for instance changed from one batch to the next batch.

This information is for instance valuable for an operator of a powder coating device if he/she does not know the exact kind of change, since operation can be continued with the old system settings if there is no change in the powder quality, whereas in case of a change of the powder quality the system settings must be corrected by an expert on the basis of experimental values.

BRIEF DESCRIPTION OF THE DRAWINGS

The invention will now be described by means of a preferred embodiment, which refers to the determination of the composition of a coating powder, with reference to the drawings.

DETAILED DESCRIPTION

Figure 1:
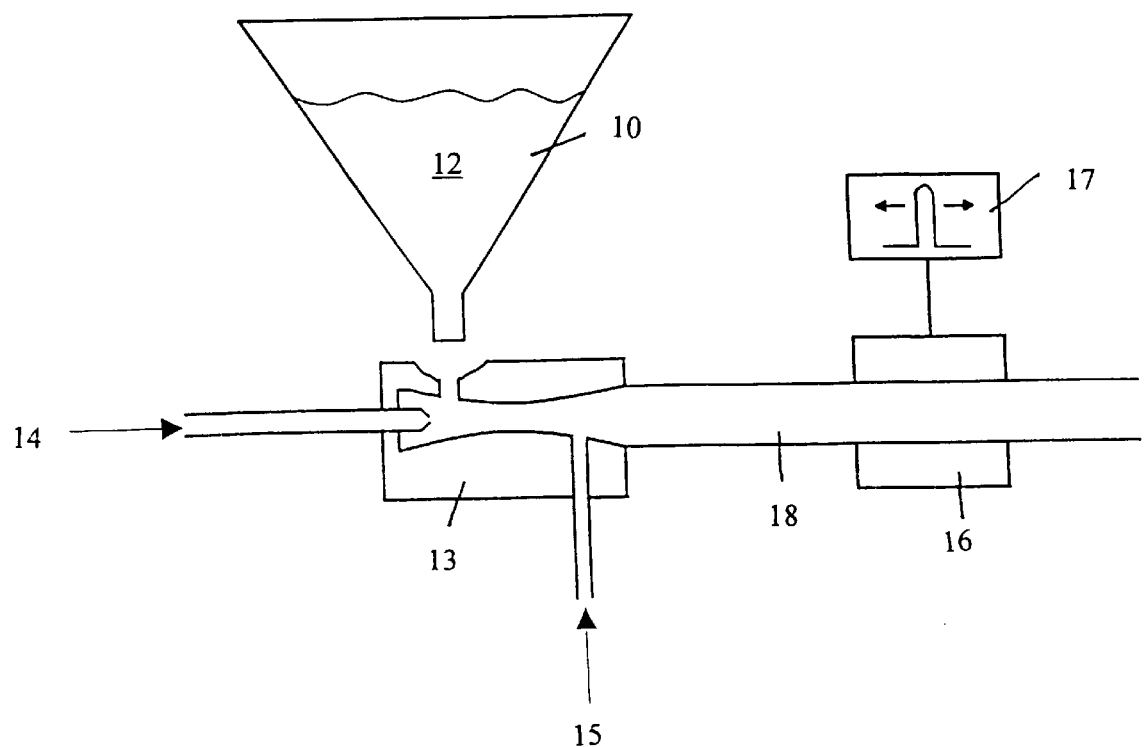
FIG. 1 is a schematical view of an inventive means for determining the composition of a coating powder.

FIG. 1 shows a funnel-like container 10 in which the coating powder 12 to be measured is located. The powder trickles at constant quantity per time from the funnel container 10 into a measuring supply injector 13 according to the hour-glass principle. The measuring supply injector 13 supplies the entire powder through a measuring line 18 and a measuring resonator device 16, which includes a high frequency resonator 36 (FIG. 2a, 2b), at precisely defined feed values of the supply air 14 and the dosing air 15. The resonator frequency of the high frequency resonator is measured and displayed on a display device 17. The resonator frequency can be displayed on the display device 17 either directly in Hz or by a different measuring value proportional thereto.

The measuring principle is described more precisely in patent applications DE 44 40 046 and DE 196 50 112.

Figure 2A:
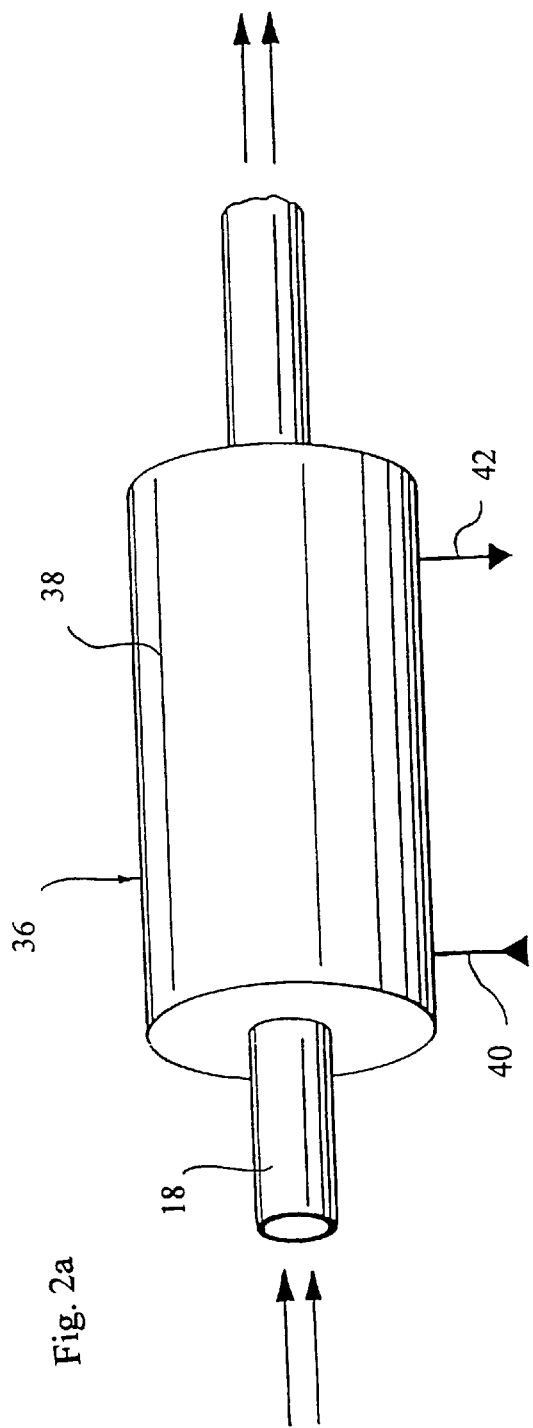
FIGS. 2a and 2b show a preferred embodiment of the measuring resonator device.
Figure 2B:
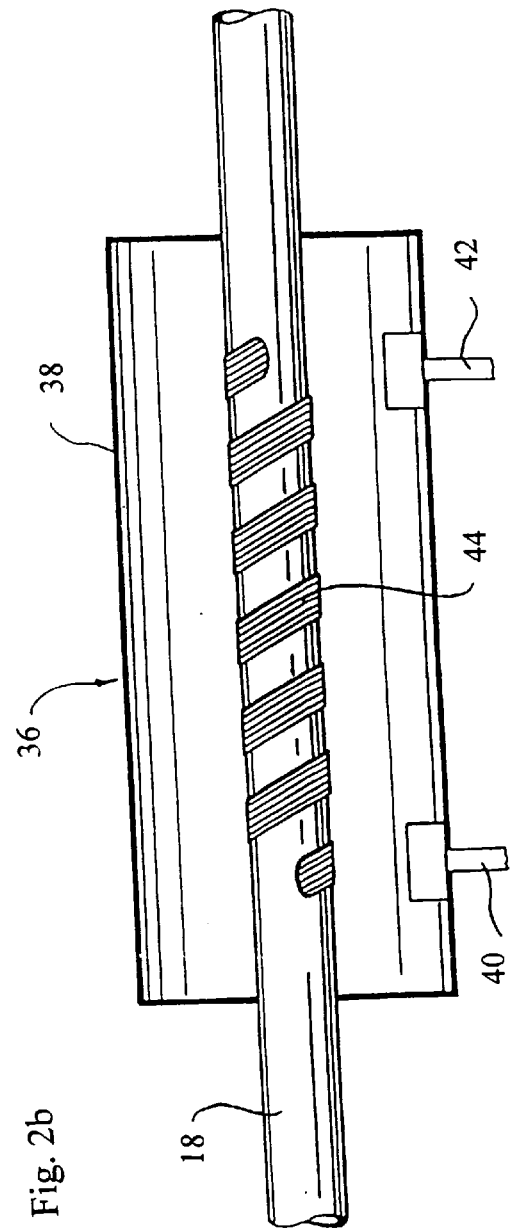

A preferred embodiment of the measuring resonator device is shown in FIGS. 2a and 2b. The measuring line 18 consists of a glass or ceramics tube, it may, however, also be a plastics hose or another supply line suitable for coating apparatus. The measuring line 18 is electrically non-conductive. It is passed by the powder flow in the direction of the arrows in FIG. 2A.

The resonator 36 comprises a metal cylinder 38 for shielding against stray fields, said metal cylinder enclosing the actual resonator portion 44. A high frequency input 40 and a high frequency output for coupling-in high frequency waves and for tapping the resonator frequency, respectively are provided at the metal cylinder 38. Coaxial cables may be connected to the high frequency in-coupling portion 40 and the high frequency out-coupling portion 42, see FIG. 2b, in order to connect the high frequency resonator to the high frequency source and a voltage sensor.

The resonator in the form of a helix or coil is located in the interior of the shielding metal cylinder 38, said resonator being wound around the measuring line 18. The high frequency resonator according to the invention can be provided as a wire coil 44 wound around the measuring line 18.

The principles of determination of the powder composition by the high frequency resonator 36 are as follows:

A part of the high frequency field generated by the resonator penetrates through the wall of the measuring line 18 in the powder flow. The resonant frequency $v_0$ of the resonator or its quality Q are measured. These magnitudes depend on the following material properties of the medium in the resonant area:

the dielectricity constant and
the absorption (loss factor).

Figure 3:
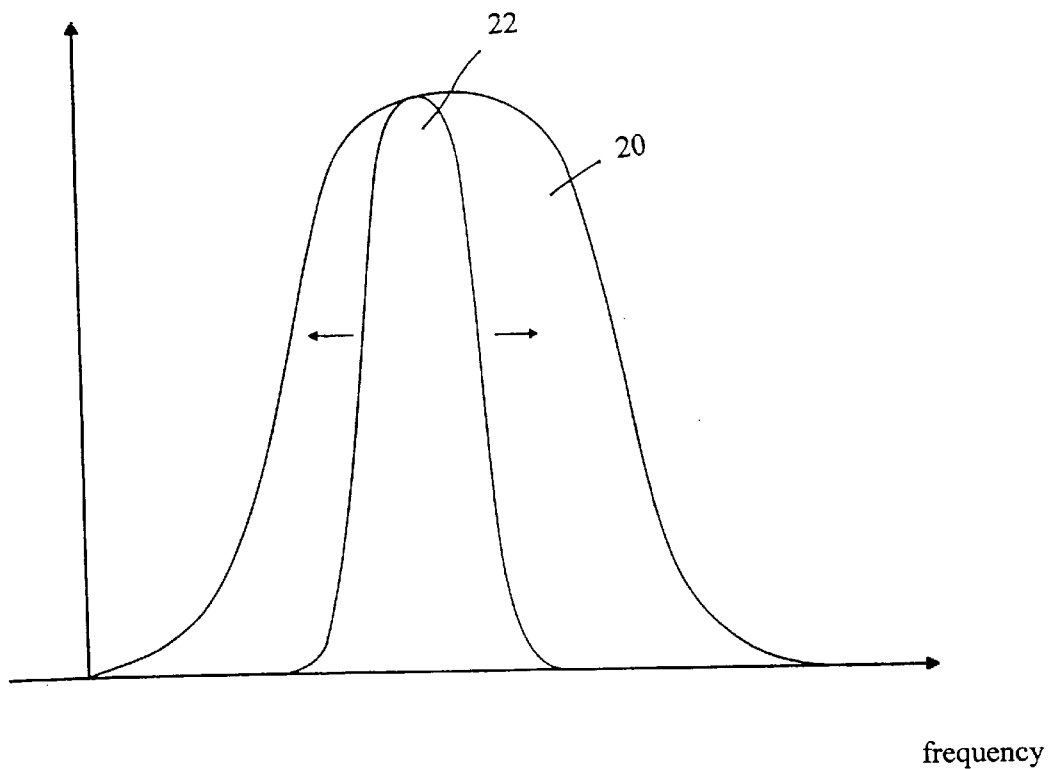
FIG. 3 shows the frequency course in the measuring resonator device.

At constant supply conditions, the change of the dielectricity constant and the absorption depend on the grain size distribution and the physical/chemical properties of the powder within the resonant area or the resonant volume, which comprises a determinable section of the measuring line 18. It result therefrom that a change of the powder quality in the resonant volume leads to a shift of the resonant frequency and to a change of the Q value and thus of the RF amplitude. A resonance curve 22 for a certain powder quality in the resonant volume is shown in FIG. 3, wherein in FIG. 3 the frequency shift that would result in case of different powder qualities is indicated by arrows without considering the change of the amplitude based on the changed quality. The curve 20 in FIG. 3 defines a working area of the high frequency resonator 36.

By measuring the resonant frequency shift or the amplitude change at different powder qualities in the resonant volume, the determination of the powder composition as a relative magnitude is possible. An absolute determination can be made by a calibration of the high frequency resonator to a reference resonant frequency and a reference amplitude for a predetermined known powder quality.

Basically, also a system without dosing air 15 can be used for performing the method of the invention as long as a supply of the powder 12 at constant conditions is ensured. The dosing air 15, however, enables to adjust the ratio of powder to air in the measuring resonator device 16 in a manner that an optimum sensitivity is achieved, since the resonator has a maximum frequency range 20 (FIG. 2) due to its geometric dimensions in which it operates at an optimum. That means that if the shift of the natural frequency is too large, if for instance a very large powder quantity is supplied through the resonator, compared to the empty resonator, the shifted amplitude of the resonance signal 22 (FIG. 2) strongly decreases and becomes too small for a reliable detection. This can be avoided by an optimum adjustment of the powder density by means of the dosing air 15.

The resonance shift in the measuring resonator device caused by the powder to be measured may also be compared to a reference resonance, which does not correspond to the empty measuring line 18 but to a reference powder mass flow.

It is also conceivable that, in particular when a different material than coating powder is to be measured, a different supply and/or dosing means is used instead of the Venturi injector 13 to generate a defined material flow. If the measuring line is arranged vertically, the dosing air could be used solely with a funnel means, such as the funnel container 12 according to the hour-glass principle, or a pump of a different supply means could be used.

It is important that the material batches to be measured and compared are supplied under defined equal conditions in order to reliably determine whether a change in composition of the material has taken place.

The features disclosed in the above description, in the claims and in the drawing can be meaningful for realizing the invention in its different embodiments either individually or in any combination.

What is claimed is:

1. A method for determining a change of composition of fluidizable solid matter particles in which the solid matter particles are fed under defined feeding conditions including a predetermined supply air flow through a measuring resonator device (16) comprising a high frequency resonator (36), and a change in at least one of the resonant frequency and high frequency amplitude of the high frequency resonator is detected in the measuring resonator device as an indication of changes being caused by the supplied solid matter particles.

2. The method as claimed in claim 1, characterized in that the detected change of the resonant frequency and/or the high frequency amplitude of the high frequency resonator are determined in relation to the respective values that are generated when the measuring resonator device is empty.

3. The method as claimed in claim 2, characterized in that the solid matter particles are fed at a predetermined rate to the supply air flow according to the Venturi principle.

4. The method as claimed in claim 1, characterized in that the solid matter particles are fed to the measuring resonator device at a predetermined rate determined by a quantity of dosing air provided to the supply air flow.

5. The method as claimed in claim 1, characterized in that the resonant frequencies of the high frequency resonator are detected and compared for a first and a second color powder test quantity fed through the measuring resonator device in order to determine a change in composition of the color powder with respect to its chemical and/or physical properties and/or its particle sizes from the first to the second test quantity.

6. Apparatus for determining a change of the composition of fluidizable solid matter particles, comprising an injector for feeding the solid matter particles to a feed air supply under defined feeding conditions, and comprising a measuring resonator device (16) including a high frequency resonator (36) disposed to receive the solid matter particles and feed air supply, to determine a change of the resonant frequency and/or of the high frequency amplitude of the high frequency resonator which is caused by the fed solid matter particles.

7. Apparatus as claimed in claim 6, characterized in that the measuring resonator device comprises a comparator disposed to provide an indication whether the resonant frequency and/or the high frequency amplitude of the high frequency resonator has changed with respect to a first test quantity when feeding solid matter particles of a second test quantity.

8. Apparatus as claimed in claim 6, characterized by a funnel device (10) for discharging the solid matter particles to the measuring resonator device (16) at a constant quantity per time unit.

9. Apparatus as claimed in claim 6, characterized in that the injector includes a Venturi injector (13) having a feed air supply (14) for supplying the solid matter particles to the measuring resonator device (16).

10. Apparatus as claimed in claim 9, characterized in that the Venturi injector (13) comprises a dosing air supply (15) disposed to control the feed of solid matter particles to the measuring resonator device.

11. Apparatus as claimed in claim 9, characterized by a control device connected to the feed air supply (14) and a dosing air supply (15) for setting a defined feed air quantity or dosing air quantity.

12. Apparatus as claimed in claim 6, characterized in that the measuring resonator device (16) comprises a measuring line (18) and the high frequency resonator (36) comprises a resonance coil which surrounds the measuring line.

13. Apparatus as claimed in claim 12, characterized in that the resonance coil (44) has a conductive structure helically attached onto the measuring line.

14. Apparatus as claimed in claim 6 in which the measuring resonator device is disposed for determining the composition of a color powder of a powder batch regarding its chemical and/or physical properties and/or its particle size compared to a reference composition.

15. The method of claim 1, characterized in that the solid matter particles comprise color powder.

16. The apparatus of claim 6, characterized in that the solid matter particles comprise color powder.

* * * * *